United States Patent [19]

Blackwell et al.

[11] 4,052,397

[45] Oct. 4, 1977

[54] PROCESS FOR THE PRODUCTION OF 2-ALKYL OR 2-CYCLOALKYL-4-METHYL-6-HYDROXYPYRIMIDINES

[75] Inventors: J. Thomas Blackwell, Greensboro; John T. Gupton, Jamestown; Jim B. Nabors, Greensboro, all of N.C.

[73] Assignee: Ciba-Geigy Corporation, Ardsley, N.Y.

[21] Appl. No.: 743,556

[22] Filed: Nov. 22, 1976

[51] Int. Cl.² ........................................... C07D 239/02
[52] U.S. Cl. ............................... 260/251 R; 424/251
[58] Field of Search ................................... 260/251 R

[56] References Cited

U.S. PATENT DOCUMENTS

| | | | |
|---|---|---|---|
| 3,703,518 | 11/1972 | Inoi et al. | 260/561 N |
| 3,997,536 | 12/1976 | Boller et al. | 260/251 R |
| 4,001,232 | 1/1977 | Groegler et al. | 260/251 R |
| 4,012,506 | 3/1977 | Balke et al. | 260/251 R |

*Primary Examiner*—Donald G. Daus
*Assistant Examiner*—Jose Tovar
*Attorney, Agent, or Firm*—Karl F. Jorda

[57] ABSTRACT

Production of 2-alkyl or 2-cycloalkyl-4-methyl-6-hydroxy pyrimidines by sequentially reacting without isolation of any intermediates in an organic solvent (1) diketene and ammonia to produce β-aminocrotonamide and (2) β-aminocrotonamide, after water removal therefrom, a lower alkanoic or cycloalkanoic acid ester and an alkali metal alkoxide.

8 Claims, No Drawings

PROCESS FOR THE PRODUCTION OF 2-ALKYL OR 2-CYCLOALKYL-4-METHYL-6-HYDROXYPYRIMIDINES

DETAILED DISCLOSURE

The present invention relates to a new and improved manufacturing process for 2-alkyl or 2-cycloalkyl-4-methyl-6-hydroxypyrimidines of the general formula

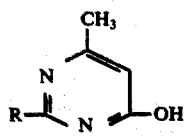

(I)

wherein R represent an alkyl or a cycloalkyl group.

Alkyl groups denoted by R and straight-chain or branched-chain groups having preferably 1 to 4 carbon atoms, such as, methyl, ethyl, n-propyl, isopropyl, n-butyl, secondary butyl, isobutyl or tertiary butyl.

Cycloalkyl groups denoted by R have 3 to 6 ring carbon atoms. Preferred cycloalkyl groups are cyclopropyl, cyclopentyl or cyclohexyl.

The compounds of formula I have particular importance as intermediates for the preparation of, e.g., phosphoric acid esters of substituted hydroxypyrimidines as disclosed and claimed in U.S. Pat. No. 2,754,243 and, in particular, O,O-diethyl-O-(2-isopropyl-4-methyl-6-pyrimidyl)-thiophosphate (DIAZINON), which has great commercial value by virtue of its well-established insecticidal and acaricidal activity and consequent usefulness in pest control.

These substituted hydroxypyrimidines have been produced in commercial practice in a laborious multi-step manner as follows:

a) Iminoether Step:

$$R-C\equiv N + C_2H_5OH + 2 HCl \longrightarrow$$

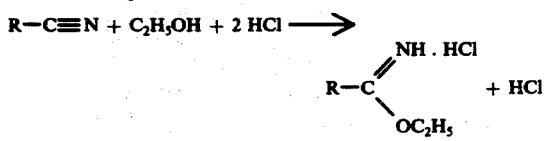

b) Amidine Step:

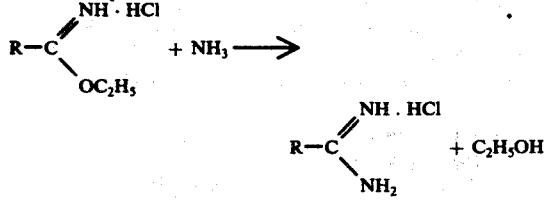

c) Ring-closure Step:

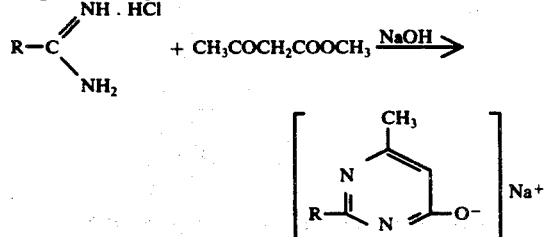

d) Neutralization Step:

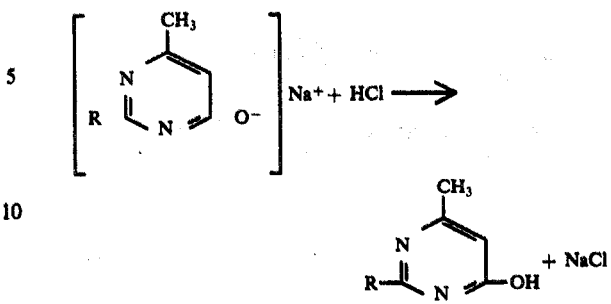

In the above formula R has the same meaning as given for Formula I.

More recently, this conventional manufacturing process has been improved and optimized by way of a continuous ring-closure/neutralization process as disclosed and claimed in U.S. Pat. No. 4,014,879, granted Mar. 29, 1977, and alternate processes for the preparation of the subject hydroxypyrimidines have been published in the Japanese patent literature.

For instance, according to Japanese Pat. No. 557,103, the subject hydroxypyrimidines can be prepared by various heat treatments from β-acylaminocrotonamides which are made from β-aminocrotonamide and acid anhydrides or acid halides and according to published Japanese Patent Application Sho 48-39,942, they can be produced by reacting β-aminocrotonamide and an organic acid ester in the presence of certain alkaline reactants, such as, alkali metals or alkali metal alcoholates. β-aminocrotonamide can be derived from diketene and ammonia by a method as described and claimed, for instance, in U.S. Pat. No. 3,703,518.

However, all of these prior art procedures leave something to be desired from the standpoint of efficient and economical large-scale commercial manufacturing.

In the search for better and cheaper process technology for the manufacture of the subject hydroxypyrimidines and the phosphoric acid ester derivatives made therefrom, it has now been found surprisingly and unexpectedly — and this forms the principal object of this invention — that these hydroxypyrimidines can be produced in a very simple manner which involves no isolation of any intermediates produced. It has been found that this can be accomplished without isolation of intermediates by reacting diketene and ammonia in a solvent and at a temperature between about −5° and 30° C, preferably 5° and 20° C, to form β-aminocrotonamide (hereinafter "BAC") in about 1 to 7 hours, which is dried, e.g., by means of azeotropic distillation or standard drying agents including molecular sieves, and then immediately converted to the desired hydroxypyrimidine by way of: (1) the addition of a solution of sodium alkoxide in an organic solvent to the solution of BAC, followed by the addition thereto of lower alkanoic or cycloalkanoic acid ester, or (2) the addition of the BAC solution to a solution of sodium alkoxide in an organic solvent, followed by the addition of lower alkanoic or cycloalkanoic acid ester. After all of the reactants are mixed, the reaction is completed by maintaining the mixture for from about 1 to 5 hours to about 20 to 50° C and preferably about 1 to 3 hours at about 40°-60° C.

The following reaction scheme illustrates the reactions taking place in this inventive process:

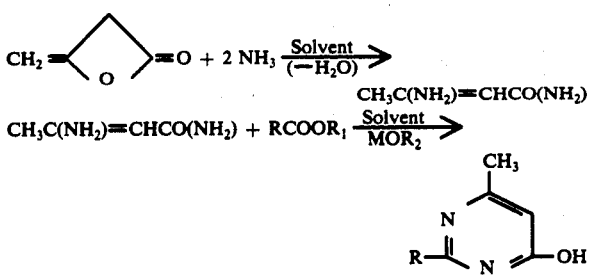

Again, R in the above formulae has the same meaning as given for formula I above, $R_1$ and $R_2$ stand for lower alkyl of up to 4 carbon atoms and M represents alkali metal.

The principal object of the subject invention is to convert BAC, produced by the reaction of diketene with ammonia without isolation, to the desired hydroxypyrimidine. The direct conversion with the concomitant elimination of the isolation step is economically advantageous because: (1) the storage of solid BAC, which tends to decompose with time, is not required; (2) the aqueous effluent which would be incurred in a filtration step is not produced; (3) equipment costs are reduced by the elimination of a filtration step, and (4) time is saved and thereby the labor and operating costs introduced by a filtration step are eliminated.

The starting materials for this inventive process, diketene and ammonia, which are commercially available are employed in a molar ratio of one mole of diketene to two or more moles of ammonia.

The organic solvent useful in this inventive process can be selected from classes which include, but are not limited to, the following: aromatic hydrocarbons, such as, benzene, toluene, xylene, cumene, ethers, such as, tetrahydrofuran, p-dioxane, 1,2-dimethoxyethane; and alcohols, such as, isobutanol, tertiary butanol; or mixtures thereof. Preferred solvents are aromatic hydrocarbons and alcohols, especially toluene, cumene and isobutanol.

It is also entirely feasible to practice the present inventive process in a semi-continuous as well as continuous fashion. Furthermore, as is shown by Example I, the process can conveniently be carried out in one reactor especially when the alkoxide and ester reactants are added to the BAC solution.

Isolation and recovery of the desired final product, the 2-alkyl or 2-cycloalkyl-4-methyl-6-hydroxypyrimidine, is carried out and effected in accordance with standard chemical procedures.

It should be understood that various changes and modifications in the procedures described above generally and exemplified below specifically can be made, such changes and modifications being within the scope of the appended claims. It should further be understood that the following examples illustrating specific embodiments are not intended to limit the disclosure.

EXAMPLE I

A one-liter four-necked, flask was equipped with a mechanical stirrer, gas dispersion tube, addition funnel, thermometer and di-butyl phthalate bubbler. Into the flask was placed toluene (200 g) and ammonia gas was bubbled through the solution for ca. 15 min. Diketene (42.0 g, 0.5 M) was added dropwise over a 1.5 hour period during which ammonia was bubbled through the reaction mixture and the temperature of the reaction was maintained between 20° and 30° C. The addition of ammonia was continued for 1.5 hours and the apparatus was fitted with a Dean-Stark water separator and condenser. Water was then removed by azeotropic distillation at reduced pressure (60–100 mm). To this mixture was added a solution of 1.11 M of sodium isobutoxide in toluene (350 ml) which had been prepared from 1.11 M of sodium hydride and 2.00 M of isobutanol. The resulting mixture was stirred and isobutyl isobutyrate (252 g, 1.75 M) was added dropwise over a 45 min. period. At the end of the addition the reaction mixture was heated at 50° C for 2 hours. The reaction mixture was then cooled in an ice-water bath and 11.3% hydrochloric acid (358.1 g, 1.11 M) was added slowly. The solvent was removed in vacuo and the solid residue was triturated with chloroform (500 ml) and filtered. The solvent was removed in vacuo from the filtrate leaving 112.99 g (59.6% by weight 2-isopropyl-4-methyl-6-hydroxypyrimidine) of solid and amounting to an 88.6% yield.

EXAMPLE II

A 500 ml, five-necked flask was equipped with a mechanical stirrer, gas dispersion tube, addition funnel, thermometer and di-butyl phthalate bubbler. Into the flask was placed isobutanol (74 g) and ammonia gas was bubbled through the isobutanol for ca. 15 min. while cooling at ca. 5° C. Diketene (42 g, 0.5 M) was added dropwise over a 1.4 hour period at 5°–19° during which the addition of ammonia was continued. The reaction mixture was stirred for 18 minutes at 40° C and this was followed by the removal of excess ammonia in vacuo (15 min). Isobutanol (10 ml) and cumene (10 ml) were added to the reaction mixture and water (9.0 ml) was removed over a three hour period by azeotropic distillation (40° C, 20–25 mm). Ammonia was then bubbled through the reaction mixture for 2.5 hours at 40°. This mixture was added in one portion to a 3-1, three-necked flask which was equipped with a mechanical stirrer and thermometer and contained a mixture of sodium isobutoxide (1.20 M), cumene (532 g) and isobutanol (106 g) under a nitrogen atmosphere. The mixture was stirred vigorously and isobutyl isobutyrate (1.20 M) was added dropwise over a 30-minute period during which the reaction temperature increased from 25° to 45° C. After the addition was completed, the mixture was stirred for 2 hours at 45° and cooled in an ice-water bath. Concentrated hydrochloric acid (109.2 g) was slowly added and the resulting mixture was subjected to the removal of solvents in vacuo. The remaining tan solid (160.23 g) contained 39.7% by weight (83.7% yield) 2-isopropyl-4-methyl-6-hydroxypyrimidine.

What is claimed is:

1. A process for the preparation of a 2-alkyl or 2-cycloalkyl-4-methyl-6-hydroxypyrimidine of the formula

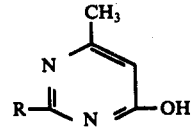

wherein R represents alkyl of 1 to 4 carbon atoms and cycloalkyl of 3 to 6 carbon atoms, which comprises sequentially reacting without isolation of intermediates in an organic solvent 1. diketene and ammonia to form β-aminocrotonamide and
2. said β-aminocrotonamide after removal of the coproduced water, with a lower alkanoic or cycloalkanoic acid ester of the formula

RCOOR$_1$ wherein R represents alkyl of 1 to 4 carbon atoms and cycloalkyl of 3 to 6 carbon atoms and R$_1$ represents lower alkyl of up to 4 carbon atoms and a metal alkoxide of the formula

MOR$_2$ wherein M is an alkali metal and R$_2$ represents lower alkyl of up to 4 carbon atoms.

2. A process according to claim 1, wherein R is isopropyl.

3. A process according to claim 1, wherein the solvent is an aromatic hydrocarbon or an alcohol.

4. A process accoring to claim 3, wherein the solvent is toluene, cumene or isobutanol or mixtures thereof.

5. A process according to claim 1, wherein the reaction temperature in the first step is between −5° and 30° C and about 20° and 90° C in the second step.

6. A process according to claim 5, wherein the reaction temperature in the first step is between about 5° and 20° C and about 40° and 60° C in the second step.

7. A process according to claim 1, wherein the metal alkoxide is sodium isobutoxide.

8. A process according to claim 1, wherein the coproduced water is removed from β-aminocrotonamide by means of azeotropic distillation under reduced pressure.

* * * * *